United States Patent
Hamazaki

(10) Patent No.: US 7,972,264 B2
(45) Date of Patent: Jul. 5, 2011

(54) PLUG BODY FOR ENDOSCOPE

(75) Inventor: Masanori Hamazaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1170 days.

(21) Appl. No.: 11/453,173

(22) Filed: Jun. 14, 2006

(65) Prior Publication Data

US 2006/0287578 A1   Dec. 21, 2006

(30) Foreign Application Priority Data

Jun. 16, 2005 (JP) ................................. 2005-176667

(51) Int. Cl.
*A61B 1/00* (2006.01)
*A61B 1/12* (2006.01)
(52) U.S. Cl. ......... 600/154; 600/159; 600/123; 604/111
(58) Field of Classification Search .......... 600/121–123, 600/153, 154, 156, 159; 604/111
See application file for complete search history.

(56) References Cited

U.S. PATENT DOCUMENTS

| 5,104,379 A * | 4/1992 | Nakamura et al. ............. 604/111 |
| 5,863,286 A * | 1/1999 | Yabe et al. .................... 600/121 |

FOREIGN PATENT DOCUMENTS

| JP | 47-37898 | 11/1972 |
| JP | 62-76145 | 5/1987 |
| JP | 3-47275 | 2/1991 |
| JP | 3-73168 | 3/1991 |
| JP | 4-329921 | 11/1992 |
| JP | 6-189899 | 7/1994 |
| JP | 2005-67666 | 3/2005 |

\* cited by examiner

*Primary Examiner* — Thomas J Sweet
*Assistant Examiner* — Ryan Henderson
(74) *Attorney, Agent, or Firm* — Scully, Scott, Murphy & Presser, P.C.

(57) ABSTRACT

An endoscope plug body comprises a plug frame, a lid member and a plug member and shuts off an inside of a treatment instrument insertion channel from an outside. The plug frame is provided with annular projection portions, a plug body destruction portion and a plug-frame destruction operation portion. A flange portion is arranged between the annular plug portions and fitted to a base of the endoscope. The plug body destruction portion and the plug-frame destruction operation portion releases the lock state by destruction. The plug frame is cylindrical and communicates with a pipe line disposed inside the endoscope. The lid member is separate from the plug frame and has a lid portion disposed at an opening at the other end of the plug frame. The plug member is separate from the plug frame, formed of an elastic member and has a plug-member treatment instrument insertion portion.

5 Claims, 11 Drawing Sheets

PLUG BODY FOR ENDOSCOPE

This Application claims benefit of Japanese Application No. 2005-176667 filed in Japan on Jun. 16, 2005, the contents of which are incorporated by this reference.

BACKGROUND OF THE INVENTION

1. Field of the Invention

The present invention relates to a plug body for an endoscope attached to a channel opening of an insertion channel of a treatment instrument provided in an endoscope which shuts off the inside of the insertion channel of the treatment instrument from an outside in an air tight manner in a state where the treatment instrument has been inserted into the channel opening.

2. Description of the Related Art

An endoscope has been widely used in the medical field or the like. Moreover, various treatments are carried out for portions, tissues or the like in a body cavity of a patient using the endoscope. Specifically, a treatment for injecting a medical solution into the body cavity of the patient by inserting a catheter into the insertion channel of the treatment instrument provided in the endoscope or treatments such as ablation or sampling of an affected portion have been carried out by inserting forceps into the insertion channel of the treatment instrument.

When carrying out these treatments using an endoscope, a catheter or forceps are introduced into the insertion channel of the treatment instrument through a plug body attached to the channel opening provided at an operation portion of the endoscope. This plug body prevents biological fluid, filth, air or the like in the body cavity from flowing back through the insertion channel of the treatment instrument due to change of a pressure in the body cavity or the like and leaking out of the channel opening to the outside.

The plug bodies are classified into a reusable type which can be reused after use and a disposable type which can not. The reusable type plug body is washed and disinfected after the use. On the other hand, once the disposable type plug body is attached to the opening of the insertion channel of the treatment instrument, removal is definitely accompanied by destruction to prohibit reuse.

Various disposable type plug bodies have been proposed.

For example, Japanese Patent Laid-Open No. 3-73168 discloses a plug body for a medical treatment instrument. In this plug body for a medical treatment instrument, an annular notch groove is formed on an outer circumferential surface of a plug frame, and the part is formed into a thin wall. And a knob of this plug body for a medical treatment instrument is constructed to integrally continue to the plug frame on the outer circumferential surface below the notch groove.

For the plug body in this construction, an operator pinches the knob with the fingers and pulls it in the circumferential direction after use, for example. Then, the plug frame is torn sequentially from the notch groove to the annular notch groove and separated into two upper and lower portions from the notch groove. By this, the plug body can be removed extremely easily from an insertion opening body.

In the meantime, Japanese Patent Laid-Open No. 3-47275 discloses a plug body for a medical instrument. In this plug body for a medical instrument, a knob is provided at a lower end of a side wall of a cylindrical part of the plug body. This knob is integrally connected to a main body part of the plug body. Notch portions are formed at the main body part corresponding to both ends of a joint of the knob and groove portions respectively connected to the notch portions are provided continuously so as to reach the part on the upper side of an annular groove portion.

With the plug body in this construction, an operator pinches the knob with the fingers and pulls it, for example. Then, the plug body is torn from the notch portions to the groove portions and a part of the annular groove portion is chipped. By this, the plug body can be easily removed from an insertion opening body.

SUMMARY OF THE INVENTION

An endoscope plug body comprises a plug frame, a lid member and a plug member and shuts off the inside of an insertion channel of a treatment instrument from an outside in an air tight manner. The plug frame is provided with lock means and destruction means. The lock means locks one end of a cylindrical base projecting on an outer surface of the endoscope by fitting from a predetermined direction. The destruction means is operated in the same direction as the fitting direction so as to release the lock state with the base by destruction. The plug frame is cylindrical and has an inner circumferential surface communicating with a pipe line arranged inside the endoscope in the fitted state. The lid member is a body separate from the plug frame and has a lid portion disposed at an opening provided at the other end of the plug frame. The plug member is a body separate from the plug frame, formed of an elastic member and has a plug-member treatment instrument insertion portion through which the treatment instrument for an endoscope to be introduced into the pipe line is inserted.

Therefore, by fitting the one end of the plug frame with the base from the predetermined direction, the endoscope plug body is locked to the base by the lock means. And when removing the endoscope plug body from the base, the plug frame is destroyed by the destruction means. Then, the lock state between the plug frame and the base is released. And by removing the plug frame from the base, the endoscope plug body can be removed from the base.

The above and other objects, features and advantages of the invention will become more clearly understood from the following description referring to the accompanying drawings.

DESCRIPTION OF THE PREFERRED EMBODIMENTS

The embodiments of the present invention will be described below referring to the attached drawings.

A first embodiment of the present invention will be described referring to FIGS. 1 to 15.

Figure 1:
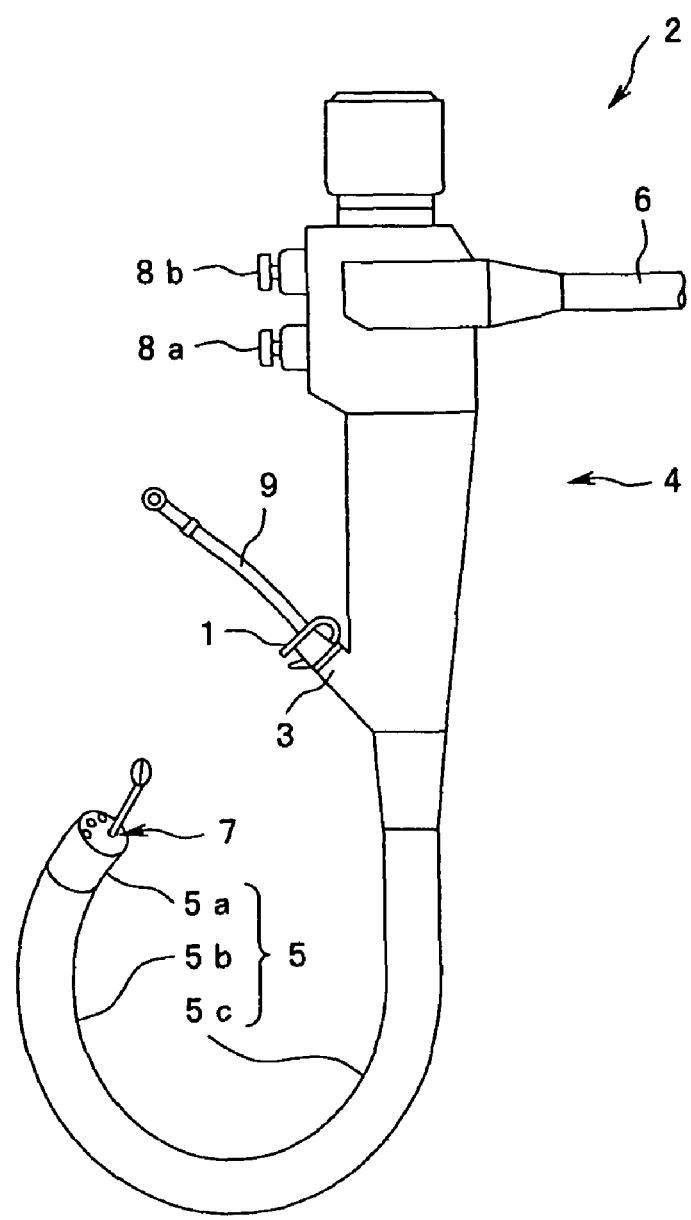
FIG. 1 is a view showing an endoscope to which an endoscope plug body is attached.

As shown in FIG. 1, an endoscope plug body 1 is to be attached to a channel opening portion 3 provided to an endoscope 2.

The endoscope 2 mainly comprises an operation portion 4 gripped mainly by an operator for operation, an elongated insertion portion 5 with flexibility, and a universal cord 6 extending from a side portion of the operation portion 4.

The insertion portion 5 comprises a tip end portion 5a, a curved portion 5b and a flexible pipe portion 5c continued sequentially from the tip end side. The operation portion 4 is provided with the channel opening portion 3 communicating with a treatment instrument insertion channel 7, which is a pipe line. Also, the operation portion 4 is provided with a curved operation knob (not shown), an air/water supply button 8a, a suction button 8b or the like. The curved operation knob is to remotely operate the curved portion 5b constituting the insertion portion 5. The air/water supply button 8a directs supply of air/water. The suction button 8b directs suction.

The endoscope plug body 1 is constituted so that air tightness between the treatment instrument insertion channel 7 and an outside is ensured for suction operation in a state attached to the channel opening portion 3.

The tip end portion 5a is provided with an observation optical system, the treatment instrument insertion channel 7, an air/water supply nozzle, an illumination optical system or the like. The insertion portion 5 has a signal cable for transmitting an image from an observation optical unit or an image guide fiber, the treatment-instrument insertion channel 7, an air/water pipe line, a suction pipe line, a light guide fiber or the like inserted and arranged inside.

The construction of the endoscope plug body 1 will be described referring to FIGS. 2 to 9.

First, the construction of the endoscope plug body 1 will be described referring to FIG. 2.

As shown in the figure, the endoscope plug body 1 mainly comprises a lid member 10, a plug member 20, and a plug frame 30. The plug member 20 is disposed in an internal space (reference character 37b in FIG. 8) provided in the plug frame 30. Reference character 3a denotes a base. The base 3a is made of metal and disposed on the opening side of the channel opening portion 3. The base 3a has a flange portion 3d at its tip end face. The flange portion 3d is a base-side lock portion and comprises an inner inclined surface 3b and an outer inclined surface 3c.

Next, the construction of the plug frame 30 will be described referring to FIGS. 2 to 9.

The plug frame 30 is formed in a substantially cylindrical shape of a resin member such as polyethylene, polypropylene or the like having somewhat elasticity. The plug frame 30 is constituted to be integrally provided with a plug-frame body portion (hereinafter abbreviated as a plug body) 31, a projection portion 32, and a lid-member mounting portion (hereinafter abbreviated as lid mounting portion) 35. The plug body 31 is mounted to the base 3a in a close contact state by press fitting by the elasticity of the plug frame 30.

The plug body 31 is, as shown in FIGS. 3 to 7, provided with a plurality of V-shaped grooves 33 on its side circumferential surface for forming thin wall portions (reference numeral 41 in FIG. 9), which will be described later. The plurality of V-shaped grooves 33 are provided with a predetermined interval, for example. The projection portion 32 is a plug-frame destruction operation portion gripped by a user when destroying the plug body 31, and constitutes the destruction means. The projection portion 32 is thicker than the plug body 31. The projection portion 32 is projected from a plug-body destruction portion 31a, which will be described later, provided on the plug body 31.

Specifically, the projection portion 32 is projected diagonally upward from the side circumferential surface of the plug body 31. The projection portion 32 is provided with a pair of V-shaped grooves 33 on both side portions at its root part. The pair of V-shaped grooves 33 are constituted as notch portions to tear the plug frame 30 open. The projection portion 32 is provided with a grip portion 32a as a support portion on the tip end side from its middle part.

The thickness of the grip portion 32a is constituted so that it gradually becomes thicker toward the tip end face, considering a gripping characteristic of a user. That is, the grip portion 32a is formed in a substantially pyramid shape with a top constituted by a plane. The tip end face of the grip portion 32a is formed as a plane portion 34. The plane portion 34 is provided with an index 34a. The index 34a indicates a load direction when the plug body 31 is to be destroyed. The index 34a is formed by a triangular shape as shown in the figure, a projection portion such as an arrow or a recess portion.

In this embodiment, the plug body 31 is destroyed when a load is applied by a user in a downward direction in the figure, as shown by the triangular index 34a, in other words, in a direction fitting with the plug frame.

The lid mounting portion 35 is constituted to project from an upper surface of the plug body 31 by a predetermined amount. The lid mounting portion 35 is provided with a lid-body mounting groove 35a on its outer circumferential portion. Reference numeral 36 is a treatment instrument guide port. The treatment instrument guide port 36 is an opening through which a treatment instrument 9 or the like is inserted and provided opposite to the channel opening portion 3.

Figure 8:
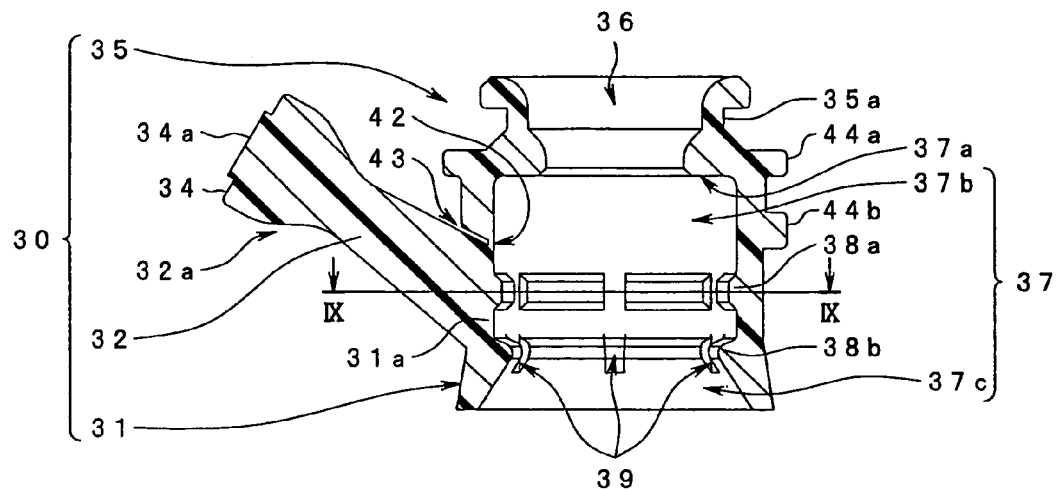
FIG. 8 is a sectional view along VIII-VIIIA line in FIG. 4 for explaining a construction of a single plug frame.

As shown in FIG. 8, the treatment instrument guide port 36 communicates with a space portion 37 through a top surface

37a. The space portion 37 comprises a plug-member inner space 37b and a base space 37c.

The plug-member inner space 37b is a space in which the plug member 20 is disposed, and the base space 37c is a space where the base 3a is disposed. Inner walls constituting the space portion 37 comprise an annular plug-member projection portion 38a, which is a first projection portion and an annular base engagement portion 38b, which is a second projection portion.

The plug-member projection portion 38a has inclined surfaces on both sides of the plane portion, for example. The base engagement portion 38b has two inclined surfaces, for example. The top portion where the two inclined surfaces are brought into contact with each other is constituted by a flat surface or a smooth curved surface. The base engagement portion 38b is arranged at the flange portion 3d of the base 3a. In that state, the base engagement portion 38b is located at the root portion of the projection portion 32.

The inclined surface on the space opening side to form the plug-body projection portion 38a is constituted to be brought into contact with the outer inclined surface 3c of the base 3a. A projection amount of the plug-member projection portion 38a is set so as to prevent the plug member 20 disposed in the plug-member inner space 37b from dropping from the plug-member inner space 37b.

Figure 9:
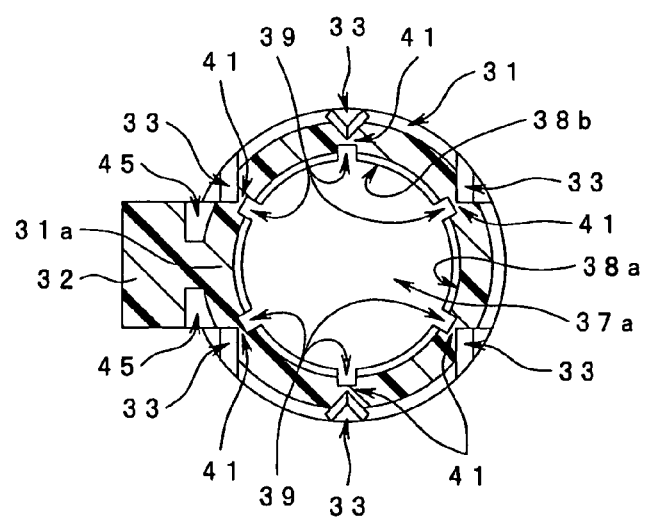
FIG. 9 is a sectional view of XI-XI line in FIG. 8.

As shown in FIG. 9, the inner wall surface of the space portion 37 is provided with a plurality of recess portions 39 opposed to the V-shaped grooves 33. By this, the plug body 31 is provided with a plurality of first thin wall portions 41 constituted by the V-shaped grooves 33 and the recess portions 39. The thickness between the first thin wall portion 41 and the opening end of the plug body 31 is formed equal to or somewhat thicker than the thin wall portion 41. The projection portion 32 is, as shown in this figure, integrally provided between the first thin wall portion 41 and the first thin wall portion 41 constituting the plug body 31.

The plug body 31 as shown in FIGS. 8 and 9 is provided with a groove 43 constituting a second thin wall portion 42 on its outer circumferential surface and on the upper surface side of the projection portion 32. The groove 43 extends in the circumferential direction. The second thin wall portion 42 is constituted to continue to the first thin wall portions 41 provided on both side surfaces of the projection portion 32. By this, in the plug body 31, a portion constituted by continuation between the first thin wall portions 41 and the second thin wall portion 42 constitutes the plug-body destruction portion 31a, which is the destruction means.

The plug body 31 is provided with an annular first flange 44a and a second flange 44b on its upper surface side. The first flange 44a and the second flange 44b constitute a ring mounting portion, which is a fitting portion. The ring mounting portion is constituted as a groove portion in which a ring portion (See reference numeral 14 in FIG. 7) constituting the base end side provided at the lid member 10 is disposed. The second flange 44b is constituted in a partially notched annular shape in the vicinity of the projection portion 32 side to prevent interference with the projection portion 32.

Reference numeral 45 denotes a notch portion for preventing a sink. In the plug frame 30, the thickness of the projection portion 32 is larger than the thickness of the plug body 31 or the lid mounting portion 35. Thus, there is a fear that a sink is generated in the projection portion 32 and a desired shape can not be obtained. By providing the notch portion 45 for preventing a sink, a flow of molten resin at molding is improved, and the projection portion 32 with the thickness having a desired rigidity can be obtained.

Figure 2:
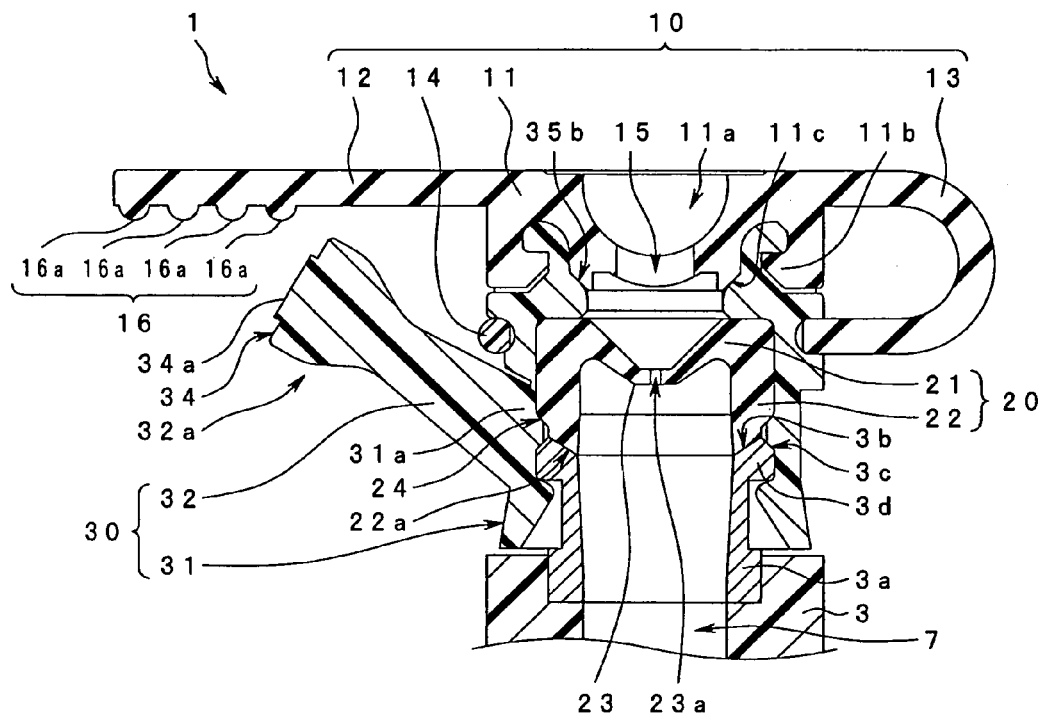
FIG. 2 is a sectional view along II-II line in FIG. 4 for explaining a construction of the endoscope plug body attached to a channel opening.

The plug member 20 shown in FIG. 2 is formed in the cylindrical shape of an elastic member such as silicon rubber, butyl rubber, natural rubber or the like. The plug member 20 is constituted with a diameter dimension and a height dimension set in advance so that the plug member 20 is accommodated and disposed in the plug-member inner space 37b.

The plug member 20 is constituted by a bottom-face constituting portion (hereinafter referred to as a bottom surface portion) 21 and an outer-circumference constituting portion (hereinafter referred to as an outer circumference potion) 22. The bottom surface portion 21 has its one face side brought into the top surface 37a. The outer circumference portion 22 projects from the bottom surface portion 21. The outer circumference portion 22 is provided with a tip-end inclined surface 22b at its tip end face. The tip-end inclined surface 22a is constituted to be brought into contact with the inner inclined surface 3b provided at the base 3a.

The bottom surface portion 21 is provided with a boundary portion 23 at its center. The boundary portion 23 is constituted in a recessed shape when seen from one side, while in a projected shape when seen from the opening side of the outer circumference portion 22. The thickness of the boundary portion 23 is formed smaller than the thickness of the outer circumference portion 22 and constituted capable of easy elastic deformation. The boundary portion 23 is provided with a round hole 23a at the center for inserting a treatment instrument, which is a plug-member treatment instrument insertion portion (hereinafter referred to as a round hole).

The round hole 23a is formed so that the treatment instrument 9 or the like can be inserted into. A diameter dimension of the round hole 23a is formed smaller than an outer diameter dimension of the treatment instrument 9 or the like to be inserted by a predetermined amount. Therefore, in the treatment instrument inserted state where the treatment instrument 9 or the like is inserted into the round hole 23a, an inner circumferential surface of the round hole 23a is brought into close contact with the outer circumferential surface of the treatment instrument 9 by the elastic force of the plug member 20 so as to hold the water and air tight states.

Also, when the treatment instrument 9 is inserted into the round hole 23a, the shape of the outer circumference portion 22 is not changed but only the boundary portion 23 formed into a thin wall is deformed. By this, the shape of the plug member 20 is maintained.

Reference numeral 24 is an inclined surface for holding. The holding inclined surface 24 is a surface with which the inclined surface provided on the plug-member inner space 37b side of the plug-member projection portion 38a is brought into contact.

The lid member 10 shown in FIGS. 2 to 7 is formed of an elastic member such as silicon rubber, butyl rubber, natural rubber or the like. The lid member 10 is integrally provided with a lid body portion 11, which is a lid portion, a knob portion 12, a connection portion 13 and a ring portion 14.

The lid body potion 11 is formed in a substantially cylindrical shape. The lid body portion 11 has a semi-spherical recess portion 11a provided at its center. The semi-spherical recess portion 11a is provided with a slit 15 for insertion of a treatment instrument, which is a lid-member treatment instrument insertion portion capable of insertion of the treatment instrument 9 or the like (hereinafter referred to as a slit) at its bottom surface. The slit 15 is brought into a close contact state by the elastic force of the lid member 10 so as to hold the water/air tight state when the treatment instrument is not inserted yet.

On the other hand, in the treatment instrument inserted state where the treatment instrument 9 or the like is inserted into the slit 15, the inner circumferential surface of the slit 15 is brought into close contact with the outer circumferential surface of the treatment instrument 9 by the elastic force of the lid member 10 so as to hold the water/air tight state.

Moreover, the lid body portion 11 is provided with a circumferential-state projection portion 11b. The circumferential-state projection portion 11b is press fitted and disposed in the lid-body mounting groove 35a provided at the lid mounting portion 35 of the plug frame 30.

The knob portion 12 is provided projecting from the outer circumference side of the lid body portion 11 in one direction by a predetermined amount so as to continue to the upper surface of the lid body portion 11. Specifically, the knob portion 12 is formed so that its tip end is located far from the plane portion 34 when it passes above the projection portion 32 in FIG. 2 projecting from the plug body 31.

A slip stopper portion 16 is provided on a lower surface at the tip end side in the figure, which is the projection portion 32 side of the knob portion 12. The slip stopper portion 16 is to prevent slip of the finger of a user gripping the knob portion 12 when opening/closing the lid member 10. The slip stopper portion 16 comprises a plurality of projections 16a, for example.

The connection portion 13 is projected from the outer circumferential side surface of the lid body portion 11 so as to continue to the upper surface of the lid body portion 11 in the other direction by a predetermined amount so that the connection portion 13 is disposed on a substantially straight line with the knob portion 12. The connection portion 13 is formed in a band state with a constant thickness dimension. The connection portion 13 is provided with the ring portion 14 formed in the annular state on its end face.

The ring portion 14 is formed with a sectional shape of a circle, a rectangle or the like. The ring portion 14 is press fitted and disposed in the ring mounting portion provided at the plug body 31.

The lid body portion 11 has a tip-end contact surface 11c. The lid mounting portion 35 has an inner circumferential contact surface 35b. A state where the circumferential-state projection portion 11b of the lid body portion 11 is press fitted and disposed in the lid body mounting groove 35a provided at the lid mounting portion 35 is referred to as the lid body portion mounted state. In this lid body portion mounted state, the tip-end contact surface 11c is in close contact with the inner circumferential contact surface 35b so as to hold the water/air tight state between the lid member 10 and the plug frame 30. Also, the outer diameter dimension of the lid body portion 11 and the outer diameter dimension of the first flange 44a are set at substantially the same diameter.

Assembling procedures of the endoscope plug body 1 will be described.

First, an operator places and arranges the plug member 20 in the plug-member inner space 37b of the plug frame 30. At this time, the plug member 20 is elastically deformed. Also, the plug member 20 is prevented from dropping from inside the plug-member inner space 37b since the plug-member projection portion 38a of the plug frame 30 is brought into contact with the holding inclined surface 24 of the plug member 20.

Figure 3:
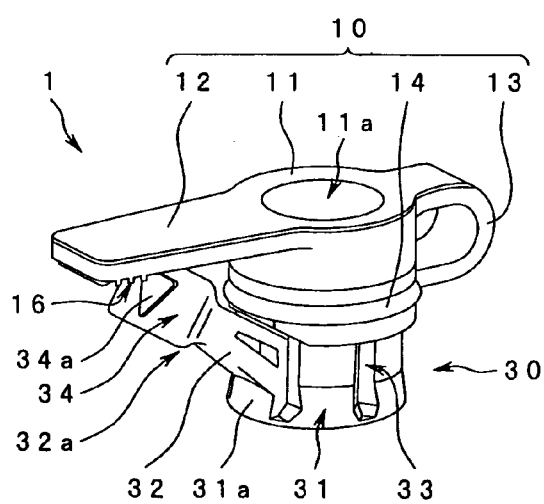
FIG. 3 is a perspective view showing an appearance of the endoscope plug body.
Figure 4:
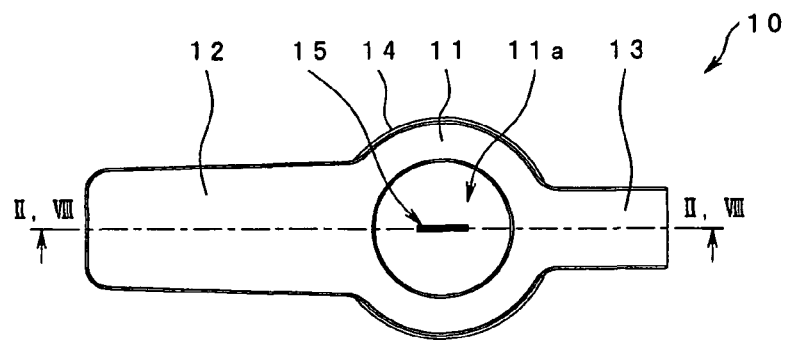
FIG. 4 is a view of the endoscope plug body in FIG. 3 seen from above.
Figure 5:
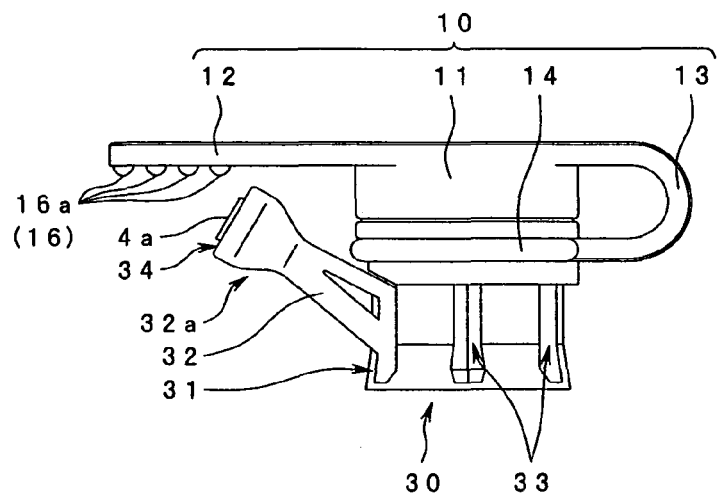
FIG. 5 is a front view of the endoscope plug body in a state where a projection portion shown in FIG. 3 is arranged on the left side.
Figure 6:
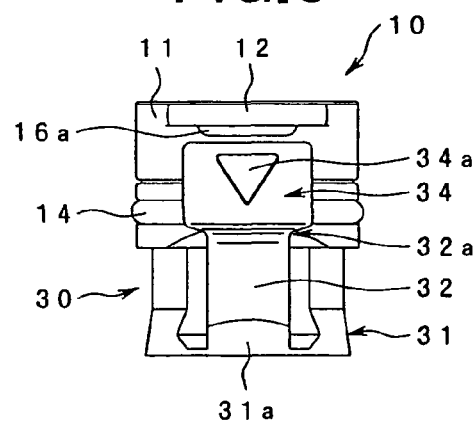
FIG. 6 is a left-side view of the endoscope plug body in a state where a projection portion shown in FIG. 3 is arranged on the front.
Figure 7:
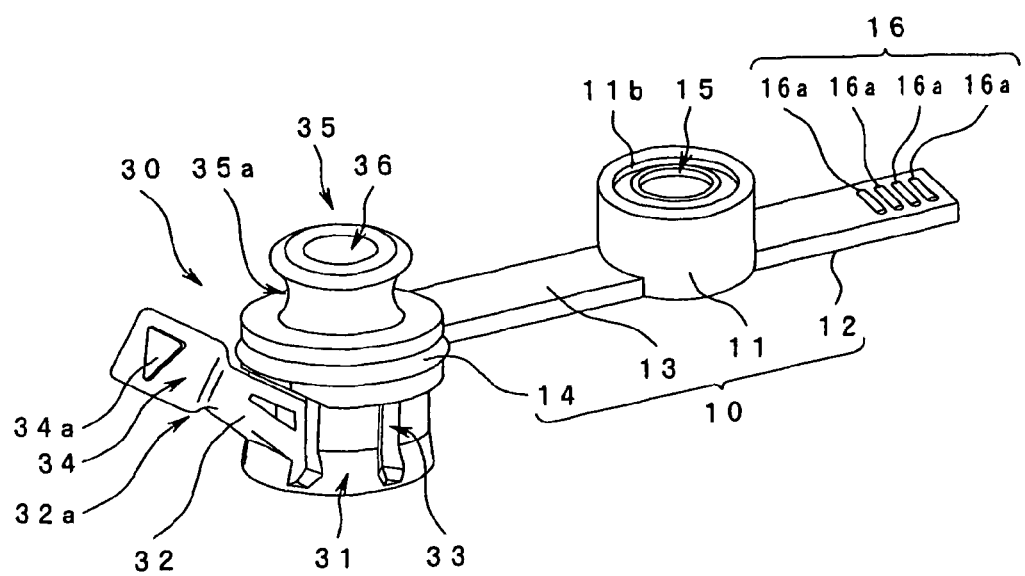
FIG. 7 is a perspective view for explaining the endoscope plug body in a state where a lid body portion of a lid member is removed from a lid member mounting portion of a plug frame.

Next, the operator press fits and arranges the ring portion 14 of the lid member 10 into the ring mounting portion comprising the first flange 44a and the second flange 44b. After that, the operator fits the circumferential-state projection portion 11b provided at the lid body portion 11 of the lid member 10 into the lid-body mounting groove 35a provided at the lid mounting portion 35 of the plug frame 30 as shown in FIG. 3 or the like. The endoscope plug body 1 shown in FIG. 7 is assembled through these procedures. The endoscope plug body 1 in the so assembled state is supplied to a user.

Next, mounting of the endoscope plug body 1 to the channel opening portion 3 will be described.

When mounting the endoscope plug body 1 to the channel opening portion 3, the user fits the opening side, which is one end portion of the plug body 31 of the plug frame 30, in the base 3a from a predetermined fitting direction. Then, the base engagement portion 38b provided at the plug body 31 and each of the thin wall portions 41 override the flange portion 3d while being elastically deformed. By this, the base engagement portion 38b is engaged and arranged in close contact with the flange portion 3d.

And the base 3a is disposed in the base space 37c, and the inner inclined surface 3b of the base 3a is brought into contact with the tip-end inclined surface 22a of the plug member 20 accommodated in the plug-member inner space 37b. Then, the plug member 20 is moved toward the top surface 37a side and the bottom surface portion 21 is brought into close contact with the top surface 37a, while the inner inclined surface 3b is brought into close contact with the tip-end inclined surface 22a. By this, the endoscope plug body 1 holds the channel opening portion 3 in the water/air tight state from the outside.

In this disposed state, the plug-member projection portion 38a is brought into contact with the outer inclined surface 3c. Therefore, when a tilting load is applied to the plug body 31, the flange portion 3d is held and fixed between the plug-member projection portion 38a and the base engagement portion 38b, and the mounting state of the endoscope plug body 1 to the channel opening portion 3 is stabilized. In other words, the plug frame 30 is disposed so that it is difficult to fall down to the channel opening portion 3 when the tilting load is applied to the plug body 31.

Moreover, in the state where the endoscope plug body 1 is mounted to the channel opening portion 3, the treatment instrument 9 or the like is inserted. At that time, the treatment instrument 9 is introduced into the channel opening portion 3 through the semi-spherical recess portion 11a, the slit 15 and the round hole 23a. In this treatment-instrument inserted state, the inner circumferential surface of the round hole 23a is brought into substantially close contact with the outer circumferential surface of the treatment instrument 9 by the elastic force of the plug member 20.

Also, the inner circumferential surface of the slit 15 is partially brought into close contact with the outer circumferential surface of the treatment instrument 9 by the elastic force of the lid member 10. That is, in the state where the treatment instrument 9 is introduced into the channel opening portion 3 through the endoscope plug body 1, a part of the inner circumferential surface of the slit 15 and the inner circumferential surface of the round hole 23a are in close contact with the outer circumferential surface of the treatment instrument 9. Therefore, in the state where the treatment instrument 9 is inserted through the endoscope plug body 1, biological fluid or filth is prevented from being dispersed to the outside.

When a treatment instrument with a large outer diameter is to be inserted into the endoscope plug body 1, the operator may insert the treatment instrument in the state where the lid body portion 11 of the lid member 10 is removed from the lid mounting portion 35 of the plug frame, 30. By this, an amount of inserting force required for insertion of the treatment instrument is reduced. In this case, the inner circumferential surface of the round hole 23a is brought into close contact with the outer circumferential surface of the treatment instrument by the elastic force of the plug member 20 and the water/air tight state is held.

Removal of the endoscope plug body 1 from the channel opening portion 3 will be described.

Figure 10:
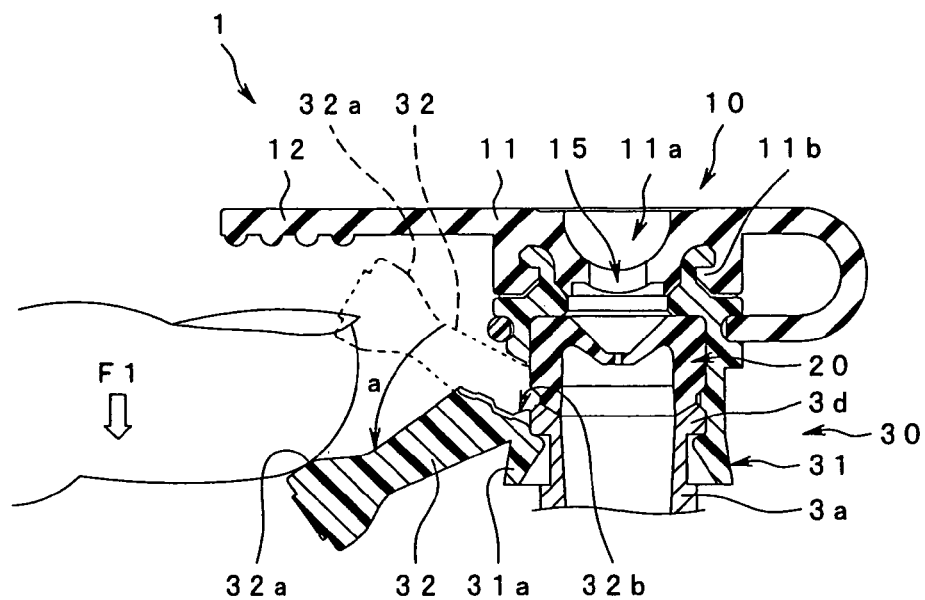
FIG. 10 is a sectional view for explaining the projection portion in a first destruction state.

When removing the endoscope plug body 1 mounted to the channel opening portion 3, the user breaks a part of the endoscope plug body 1, more specifically, the plug-body destruction portion 31a, which is a part of the plug body 31. At that time, the user arranges the forefinger, for example, on the upper surface of the grip portion 32a of the projection portion 32, as shown in FIG. 10. At this time, if the knob portion 12 is in the way, the knob portion 12 is raised and moved by the nail side.

And the user applies a downward load to the projection portion 32 as shown by an arrow F1, in other words, in a direction to fit the endoscope plug body 1. Then, the projection portion 32 is rotationally moved by the load applied by the user in a direction shown by an arrow a with a portion where the base engagement portion 38b is in contact with the flange portion 3d as its fulcrum.

At this time, a stress generated by the projection portion 32 concentrates on the second thin wall portion 42 in the vicinity of the projection portion 32 and the first thin wall portion 41. The base 3a is made of metal and has a high rigidity. Therefore, the flange portion 3d of the base 3a is not crushed and the plug body 31 is prevented from being crushed inward, which would lead to dispersion of the load.

Figure 11:
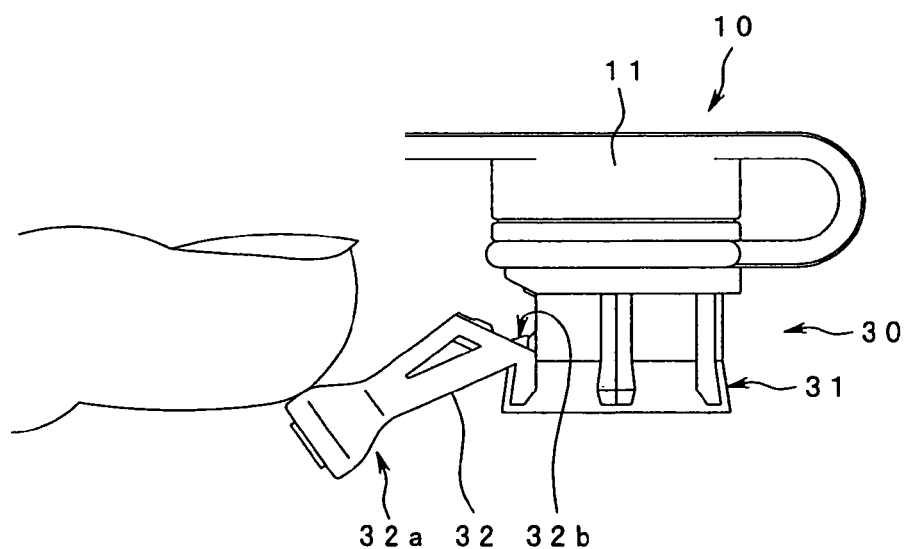
FIG. 11 is an appearance view in the first destruction state in FIG. 10.

And by the stress generated by the projection portion 32, the projection portion 32 is broken, first from the second thin wall portion 42 provided on the upper surface side. After that, the first thin wall portions 41 provided on both sides of the plug-body destruction portion 31a integral with the projection portion 32 are broken from the second thin wall portion 42 side. At this time, the plug-body destruction portion 31a integrally provided with the projection portion 32 is not fully separated from the plug body 31, but a part of the plug-body destruction portion 31a is connected by a predetermined amount. Therefore, as shown in FIG. 11, the apparent destruction state of the plug body 31 is such that the root portion 32b of the projection portion 32 is bent. This destruction state is referred to as a first destruction state.

Figure 12:
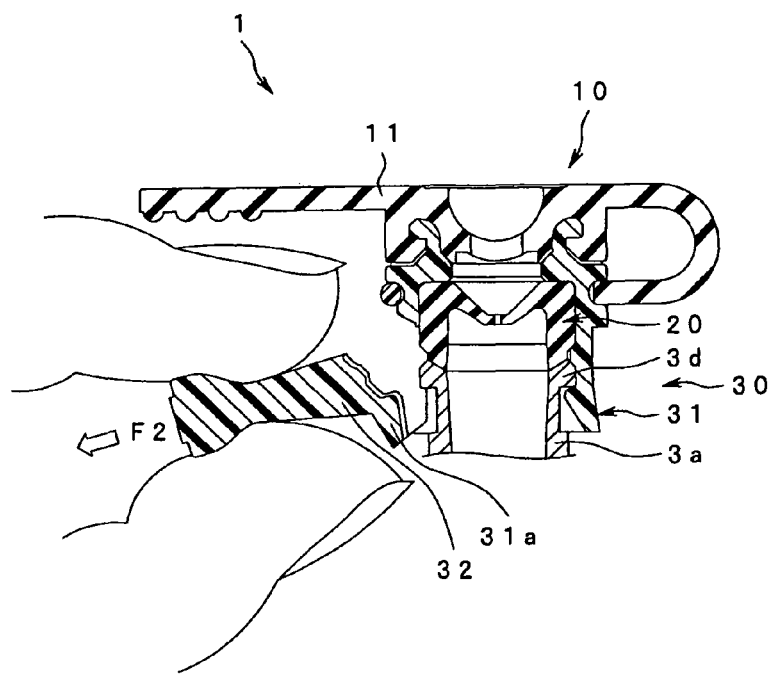
FIG. 12 is a sectional view for explaining the projection portion in a second destruction state.
Figure 13:
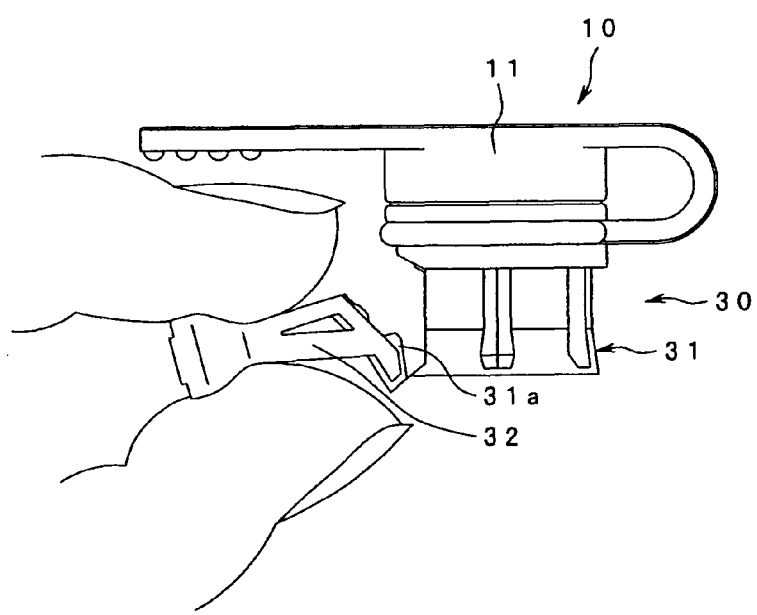
FIG. 13 is an appearance view in the second destruction state in FIG. 12.

After the first destruction, as shown in FIGS. 12 and 13, the user grips the grip portion 32a of the projection portion 32 with the thumb and the forefinger, for example. And the user applies a diagonally downward load as shown by an arrow F2 to the projection portion 32. Then, the thin wall portions 41 which were not fully broken by the first destruction are completely destroyed. By this, the plug-body destruction portion 31a together with the projection portion 32 are brought into the destruction completed state where they are fully separated from the plug body 31 and destroyed. This destruction state is referred to as a second destruction state.

In this second destruction state, the endoscope plug body 1 from which the plug-body destruction portion 31a and the projection portion 32 are separated is still mounted, not removing from the channel opening portion 3. That is because a force is not applied in a direction where the plug body 31 is removed from the channel opening portion 3 since the projection portion is broken toward the channel opening portion 3.

After that, the user takes out the endoscope plug body 1 mounted to the channel opening portion 3. At that time, the endoscope plug body 1 is removed by the hand of the user smoothly from the channel opening portion 3. That is because the plug-body destruction portion 31a is separated from the plug body 31 and the plurality of first thin wall portions 41 are provided at the plug body 31.

In this way, a plug-body destruction portion comprising thin wall portions is provided at a part of a plug body provided at a plug frame constituting an endoscope plug body. In addition, a projection portion is provided at this plug-body destruction portion. By this, by operating the projection portion with a slight force amount as appropriate, the plug-body destruction portion can be separated from the plug body without dropping the endoscope plug body from the channel opening portion.

Therefore, the user can remove the endoscope plug body from which a part of the plug body has been separated smoothly from the channel opening portion. Also, the plug-body destruction portion, which is a part of the plug body has been destroyed. Thus, such a work error that the user makes wrong determination from the appearance on whether the endoscope plug body has been used or not and reuses an used endoscope plug body by mistake can be surely prevented. Therefore, a new endoscope plug frame is surely attached to a channel opening portion for each case.

Also, the user has applied a load to press the projection portion downward, in other words, moved the finger to the operation portion side of the endoscope to perform primary destruction of a part of the plug body. Thus, in the case where a load by the finger tip is removed at once, the finger of the user is prevented from hitting the periphery with a great force when the finger is removed from the projection portion.

Moreover, the plug body destruction portion provided at the frame body is a structure of destruction in two steps of the first destruction state and the second destruction state. And when the primary destruction with a large load applied is completed, the projection portion continues to the plug body. Therefore, drop of only the projection portion can be prevented.

Furthermore, since a partial side face of the plug body is destroyed, the plug body can be held at the channel opening portion in the second destruction state with an original shape as a structural body substantially remains. Therefore, drop of the plug member or the like with adhesion of biological fluid or filth can be prevented, and work can be carried out hygienically.

Furthermore, the grip portion of the projection portion is constituted in a pyramid shape. By this, the user can pull the projection portion by holding the upper and the lower parts or the right and the left parts with the fingers. That is, the user can surely complete the second destruction with easily applying a load.

It is to be noted that the user can also perform destruction operation by holding with the thumb at the projection portion and the other fingers on the operation portion of the endoscope. In that case, since the user can perform destruction operation with one hand, workability is improved.

Moreover, the projection portion is projected upward of the lid. Therefore, the user can perform destruction operation only in the downward direction, that is, in the channel opening direction and can not apply a force in such a direction to allow the plug body to drop from the channel opening.

Figure 14:
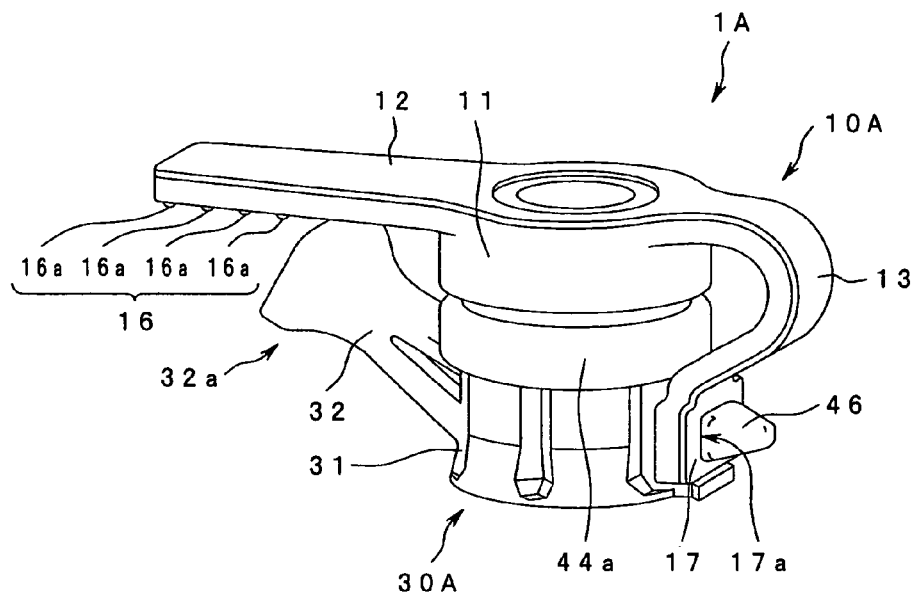
FIG. 14 is a perspective view showing an appearance of the plug body for the endoscope of another construction.

Furthermore, the medical endoscope plug body can be constituted as shown in FIG. 14. In a medical endoscope plug body 1A shown in FIG. 14, constructions of a lid member mounting portion in a plug frame 30A and a ring portion of a lid member are different from those of the above. That is, as shown in the figure, the endoscope plug body 1A is provided with an arrowhead shaped portion 46, which is a fitting portion on a lower part on the side opposite to the side where the projection portion 32 of the plug frame 30A is formed.

The arrowhead shaped portion 46 is in a rectangular shape formed larger toward the base end side, and the most base end side is contrarily formed in an elongated quadratic prism shape. A lid member 10A has a flat portion 17 constituting the base end side portion integrally with the connection portion 13. The flat portion 17 is provided with a square hole 17a at its substantially center with the size equal to the quadratic prism. The square hole 17a is arranged in the attached state after being elastically deformed along the arrowhead shaped portion 46. At the plug body 31 of the plug frame 30A, there is no distinction between the first flange 44a and the second flange 44b as in the first embodiment, but a single flange portion 44c is formed. The other constructions are the same as those of the above-mentioned embodiment, and the same reference numerals are given to the same members, whose description will be omitted.

In this way, the medical endoscope plug body 1A of this embodiment, there is no ring portion at the lid member. Thus, when the endoscope plug body 1A is to be assembled by an automatic machine, intertwining of parts with each other is prevented, and members are easily arranged by a part feeder. Therefore, the medical endoscope plug body 1A is suitable for mass production through assembling by an automatic machine, which leads to cost reduction.

Figure 15:
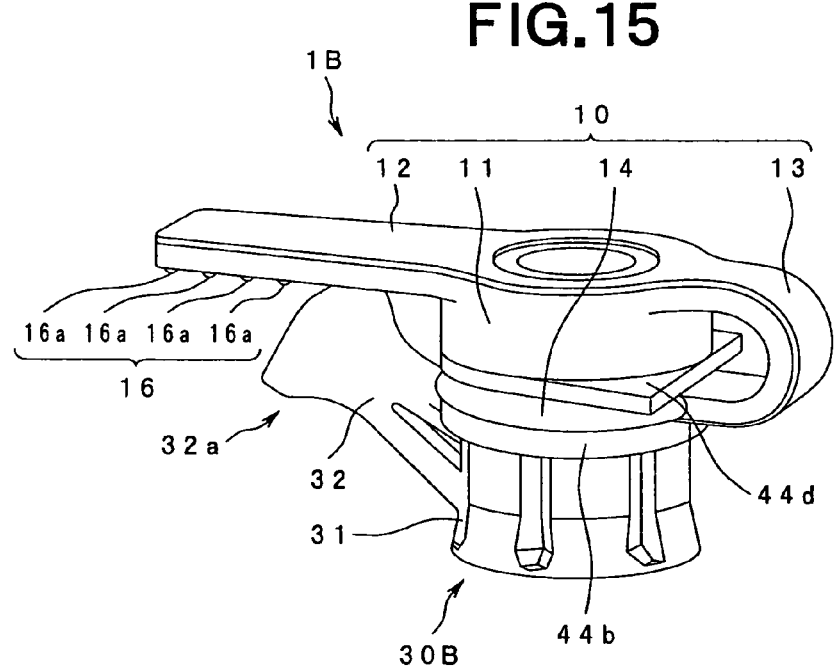
FIG. 15 is a perspective view showing an appearance of the endoscope plug body of still another construction.

Or, the endoscope plug body may be constituted as shown in FIG. 15. In an endoscope plug body 1B shown in the figure, a drop stopper fin 44d constituting a fitting portion is provided at a portion of the first flange 44a. By this, when the lid body portion 11 is removed from the lid mounting portion 35 and pulled upward strongly, the ring portion 14 is hooked by the drop stopper fin 44d due to provision of the drop stopper fin 44d, which prevents the lid member 10 from being separated from the plug frame 30B inadvertently and opening/closing of the lid body portion 11 is made easier.

A second embodiment of the present invention will be described referring to FIGS. 16 to 19.

Figure 16:
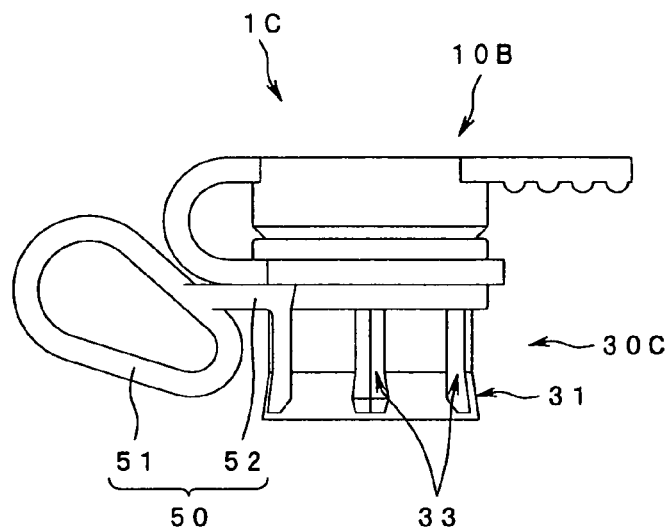
FIG. 16 is a view showing the endoscope plug body provided with a plug frame having a plug body destruction ring.
Figure 17:
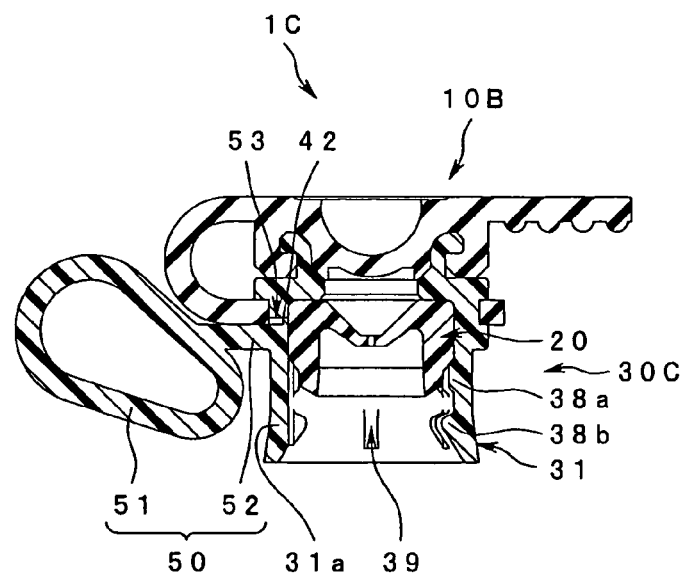
FIG. 17 is a sectional view for explaining a construction of the endoscope plug body.
Figure 18:
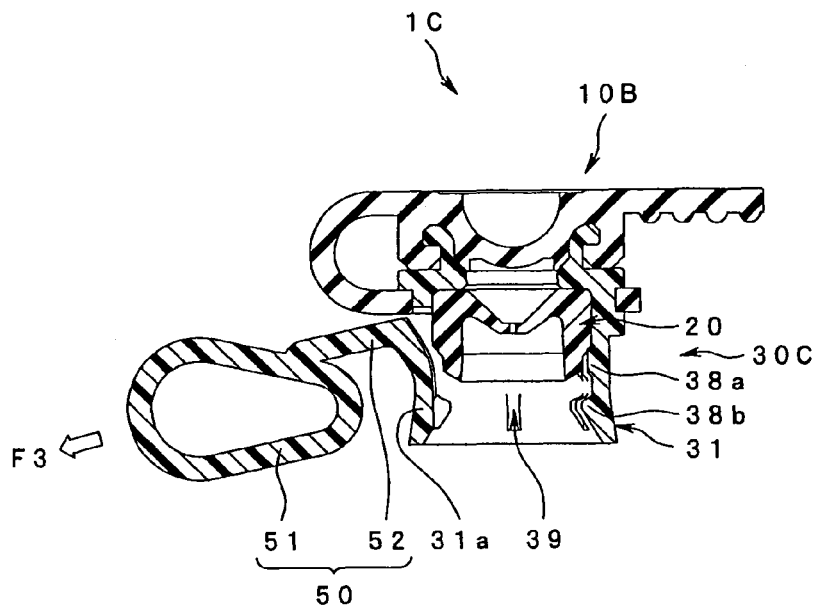
FIG. 18 is a view showing a state where the plug body destruction portion is destroyed by applying a load to the plug body destruction ring.
Figure 19:
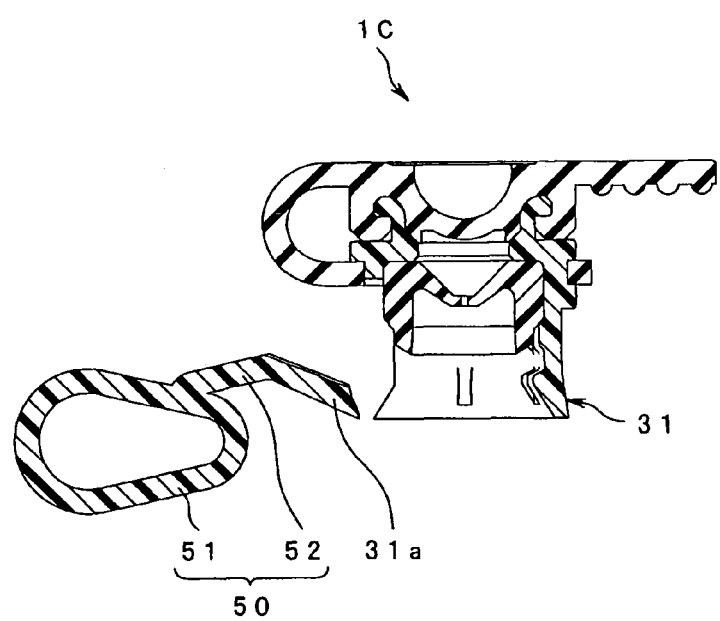
FIG. 19 is a view showing a destruction completed state where a part of the plug body is separated.

An endoscope plug body 1C of this embodiment has the same construction as that of the first embodiment for a plug frame 30C except a part thereof. As for the lid member 10B, the length of the knob portion 12 is short and a sectional shape of the ring portion 14 is rectangular. And as shown in FIGS. 16 and 17, in the plug frame 30C in this embodiment, the construction of a portion corresponding to the projection portion 32 in the above first embodiment and its periphery is different. Specifically, in the plug frame 30C, a plug-body destruction ring portion 50 as a plug frame destruction operation portion instead of the projection portion 32 is integrally provided at the plug body destruction portion 31a.

The plug-body destruction ring portion 50 comprises a ring portion 51 and a connection portion 52. The ring portion 51 is constituted so that the finger of a user or the like can be hooked. The connection portion 52 is in the band state and integrally constituted with the ring portion 51. The connection portion 52 is projected in exactly the lateral direction from a middle portion of the plug body destruction portion 31a provided at the plug body 31.

In this embodiment, too, the first thin wall portion 41 similar to that of the first embodiment is formed on both sides at a part connecting the connection portion 52 to the plug body 31. Moreover, the connection portion 52 is provided with a notch 53 on its upper part. The notch 53 is formed to the position of the first thin wall portions 41 on the both sides. The thickness dimension of the connection portion 52 is constituted so that the connection portion 52 is not torn off even if the user pulls it in a direction shown by an arrow F3 with a predetermined load. It is to be noted that the position where the notch 53 is formed is set so that a stress is concentrated in the vicinity of the root part of the connection portion 52.

The knob portion 12 of the lid member 10B in this embodiment prevents interference with the ring portion 51 of the plug-body destruction ring portion 50. Specifically, the position of the knob potion 12 is set to be opposed to the ring portion 51 with the center axis of the plug frame 30C between them, for example, by changing the mounting position of the lid member 10B to the plug frame 30.

The other constructions are the same as those of the first embodiment, and the same reference numerals are given to the same members, whose description will be omitted.

In this embodiment, when removing the endoscope plug body 1C from the channel opening portion 3, the user hooks the finger in the ring portion 51 of the plug-body destruction ring portion 50. And the user pulls the plug-body destruction ring portion 50 in the arrow direction with the load F3. Then the load concentrates at the upper end of the first thin wall portion 41 at the upper end root of the connection portion 52 where the notch 53 is provided. Here, the user continues to apply the load F3 with the finger hooked in the ring portion 51. Then, the first destruction state is brought about. After that, a load smaller than the load F3 which has been continuously applied is given. By this, destruction of the first thin wall portion 41 progresses, the plug-body destruction ring portion 50 separates the plug-body destruction portion 31a from the plug body 31, which is the second destruction portion.

In this way, the plug-body destruction ring portion having a finger hook ring is provided at the plug body destruction portion constituting the plug body. By this, the user can easily destroy the plug-body destruction portion, which is a part of the plug body, by a tensile load by hooking the finger in the finger hook ring.

Figure 20:
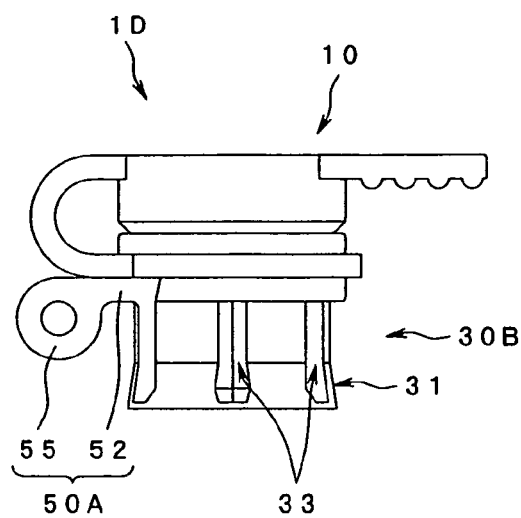
FIG. 20 is a view for explaining a variation of the endoscope plug body.
Figure 21:
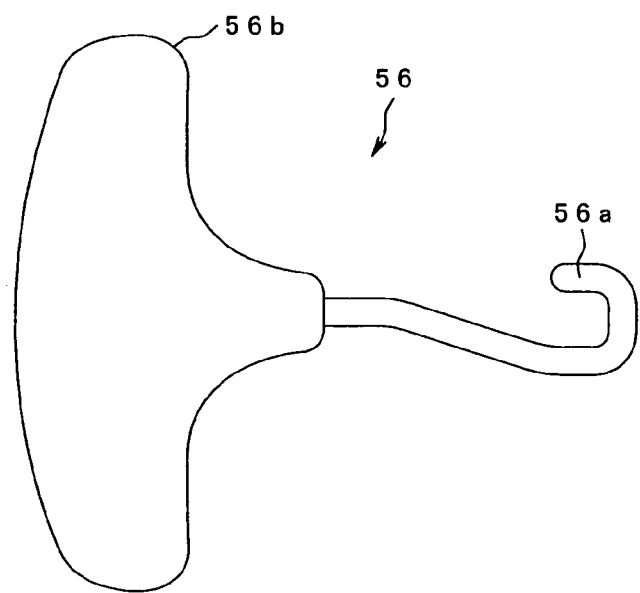
FIG. 21 is a view showing a construction example of a jig for destruction.

Instead of the ring portion 51, a jig arranging ring 55 may be provided at the connection portion 52 as shown in FIG. 20 so as to constitute an endoscope plug body 1D having a plug-body destruction ring portion 50A. By this, a bent portion 56a of a destruction jig 56 having a grip portion 56b shown in FIG. 21 is disposed in the jig arranging ring 55, and the load F3 is applied to the plug-body destruction ring portion 50A by gripping the grip portion 56b in this state. By this, the plug body destruction portion, which is a part of the plug body, can be destroyed more easily.

Having described the embodiments of the invention referring to the accompanying drawings, it should be understood that the present invention is not limited to those precise embodiments and various changes and modification thereof could be made by one skilled in the art without departing from the spirit of scope of the invention as defined in the appended claims.

What is claimed is:

1. An endoscope plug body for shutting off an inside of a treatment instrument insertion channel of an endoscope from an outside, the endoscope plug body comprising:
   a plug frame comprising:
      a plug-frame body portion comprising:
         a base space in which a base is to be located, the base being projected on an outer surface of the endoscope;
         a plurality of first thin wall portions configured by V-shaped grooves and recess portions provided on an inner circumferential surface opposed to the V-shaped grooves, the plurality of first thin wall portions being provided at a predetermined interval and configured to elastically deform so as to be fitted to the base; and a first projection portion and a second projection portion, the second projection portion being disposed at a first end of the plug frame, the first and second projection portions being provided on the inner circumferential surface of the base space and holding and fixing a base side engagement portion, the inner circumferential surface communicating with the treatment instrument insertion channel of the endoscope in a state in which the base side engagement portion is fitted between the first projection and the second projection portion; and a plug-frame destruction operation portion which is integrally connected with the plug-frame body portion and projecting in a direction diagonally away from the first end of the plug frame from a side circumferential surface of the plug-frame body portion;

the plug-frame body portion further comprising a plug-body destruction portion comprising:

two first thin wall portions of the plurality of first thin wall portions, the two first thin wall portions being located on both sides of a root portion of the plug-frame destruction operation portion; and a second thin wall portion located on a side closer to a top surface than the first projection portion, the second thin wall portion including a groove formed on an upper surface of the root portion and extending in a circumferential direction so as to continue to the two first thin wall portions;

a lid member, separate from the plug frame, and comprising a lid portion disposed at an opening provided at a second end of the plug frame; and a plug member, separate from the plug frame, and arranged within the inner circumferential surface of the plug frame, the plug member having elasticity and defining a plug-member treatment instrument insertion portion through which an endoscope treatment instrument to be introduced into the channel is inserted;

wherein the second thin wall portion and the second thin wall portion-side of the two first thin wall portions of the plug-body destruction portion are destructed by the plug-frame destruction operation portion being rotationally moved using a contact portion of the second projection portion and a contact portion of the base side engagement portion as a fulcrum, by a load which is applied to the plug-frame destruction operation portion and is in an approximately same direction as when fitting the base space to the base side engagement portion.

2. The endoscope plug body according to claim 1, wherein the plug-frame destruction operation portion destructs the first thin wall portion in a non-destructed state by a load applied to the plug-frame destruction operation portion in a combined direction of a radially outward direction with respect to a circumferential wall of the plug-frame body portion and a direction of fitting the base space with the base, to separate the plug-body destruction portion from the plug-frame body portion.

3. The endoscope plug body according to claim 1, wherein the plug frame is provided with a fitting portion to which a base end portion of the lid member is detachably mounted.

4. The endoscope plug body according to claim 1, wherein the lid member is formed of an elastic member and has a lid-member treatment instrument insertion portion into which an endoscope treatment instrument to be introduced into a pipe line is inserted at the lid portion.

5. The endoscope plug body according to claim 1, wherein the plug frame has an inner space in which the plug member is disposed.

* * * * *